(12) United States Patent
Hsiao

(10) Patent No.: US 6,416,466 B1
(45) Date of Patent: Jul. 9, 2002

(54) STRUCTURE FOR VAGINA SPECULUM

(76) Inventor: Ray-Ling Hsiao, 4F, No. 12, Aly. 15, Ln. 175, Sec. 2, Ho-Ping E. Rd., Taipei (TW)

( * ) Notice: Subject to any disclaimer, the term of this patent is extended or adjusted under 35 U.S.C. 154(b) by 0 days.

(21) Appl. No.: 09/818,552

(22) Filed: Mar. 28, 2001

(51) Int. Cl.$^7$ ................................................ A61B 1/32
(52) U.S. Cl. ...................................................... 600/220
(58) Field of Search ................................ 600/219, 220, 600/221, 222, 223

(56) References Cited

U.S. PATENT DOCUMENTS

| | | | | |
|---|---|---|---|---|
| 563,236 A | * | 6/1896 | Penhall | 600/220 |
| 888,484 A | * | 5/1908 | Gehorsam | 600/219 |
| 1,060,350 A | * | 4/1913 | Miller | 600/219 |
| 1,894,725 A | * | 1/1933 | Bacon | 600/220 |
| 3,470,872 A | * | 10/1969 | Grieshaber | 600/219 |
| 3,817,242 A | * | 6/1974 | Uddenberg | 600/222 |
| 4,385,626 A | * | 5/1983 | Danz | 600/220 |
| 5,785,648 A | * | 7/1998 | Min | 600/220 |
| 5,891,017 A | * | 4/1999 | Swindle et al. | 600/219 |
| 5,899,854 A | * | 5/1999 | Slishman | 600/219 |
| 5,997,474 A | * | 12/1999 | Batchelor | 600/220 |

* cited by examiner

*Primary Examiner*—Paul J. Hirsch
(74) *Attorney, Agent, or Firm*—Troxell Law Office PLLC

(57) ABSTRACT

An improved structure for Vagina Speculum, which mainly consists of a first body and a second body which are set two jaws with thin and flat figure and concave surfaces on front ends of the first body and the second body. The first body pivotally joints the second body, and there is a matching structure installed on the first body and the second body that gently held by user to fast stretch and fasten the two jaws on the front ends of the first body and the second body. The invention focuses the matching structure to be improved for better releasing function, therefore, the matching structure can be rapidly released after operation, and the improved structure is then more convenient for moving out from patient's vagina and more practical.

9 Claims, 11 Drawing Sheets

STRUCTURE FOR VAGINA SPECULUM

FIELD OF THE INVENTION

The invention is an improved structure for a Vagina Speculum, especially for a Vagina Speculum that can be rapidly stretched, fastened and released.

BACKGROUND OF THE INVENTION

Vagina Speculum has been used very often in clinic service of Department of Gynecology and Obstetrics. Most of Medical Doctors have to open vagina for inspection via Vagina Speculum, and therefore the health conditions of vagina and the surrounding organs, ex. cervix, can be clearly identified by Doctors after inspections. Hence, correct treatment can be made for patients. The prior art of Vagina Speculum mainly consists of two upper and lower jaws A and B with a pivotal joint. Each jaw comprises a forward nose of forward portion of jaw, a handle of rear portion of jaw and a locking bar C adjusting the distance between the two jaws, wherein one end of the locking bar C is set a penetrating hole (not shown in figure), and the other end is with several screw threads D and two parallel, closely spaced axially-oriented mounting plates E positioned perpendicularly from the inner surface of midway of handle of jaw B. A transverse pivoting axle G goes through a bearing hole F on mounting plate E, and continuously protrudes the said penetrating hole on locking bar C, then fixes locking bar C pivotally on mounting plate E. The end of locking bar C with screw threads D goes through a locking aperture H on the rear portion of handle of jaw A, and an adjusting knob I is fastened on screw threads D. By means of regulating adjusting knob I back and forth, Vagina Speculum is then opened smaller and larger. The merits for the foresaid structure, by way of screw threads D to regulate and fasten, are with the certain fastening and the stepless fastening. On the other hand, not only the fastening for stretching, but also releasing for closing, both need to regulate adjusting knob I continuously, and it is inconvenient and slow for operation.

To learn from the above mentioned, although the prior art is with the merit of rapidly stretching open, the fastening and closing must still be improved.

SUMMARY OF THE INVENTION

The first object of the invention is to offer an improved structure for vagina speculum made of metal which can be sterilized or disposable plastic. The improved structure consists of upper jaw 11 and lower jaw 21 of thin material forming an internal concave profile of a first body 1 and a second body 2. The first body 1 joints with the second body 2 pivotally. A buckling structure 3 is set on the first body 1 and the second body 2, which is held by user to rapidly stretch and fasten front ends of upper jaw 11 and lower jaw 21 of first body 1 and second body 2. The tremendous feature of the invention focuses on improving the buckling structure 3 for better releasing function, and thus buckling structure 3 can be quickly released after operating.

The second object of the invention is to offer an improved structure for a vagina speculum, wherein the end part of the lower jaw 21 is extended, whereby a patient's secretion can be exhausted along the extended end part for avoiding contact with the Doctor's hands.

To further understand the structure objects and functions of the invention for investigation committeemen, reference is made to the figures for detail description.

DETAILED DESCRIPTION OF THE PREFERRED EMBODIMENT

Figure 1:
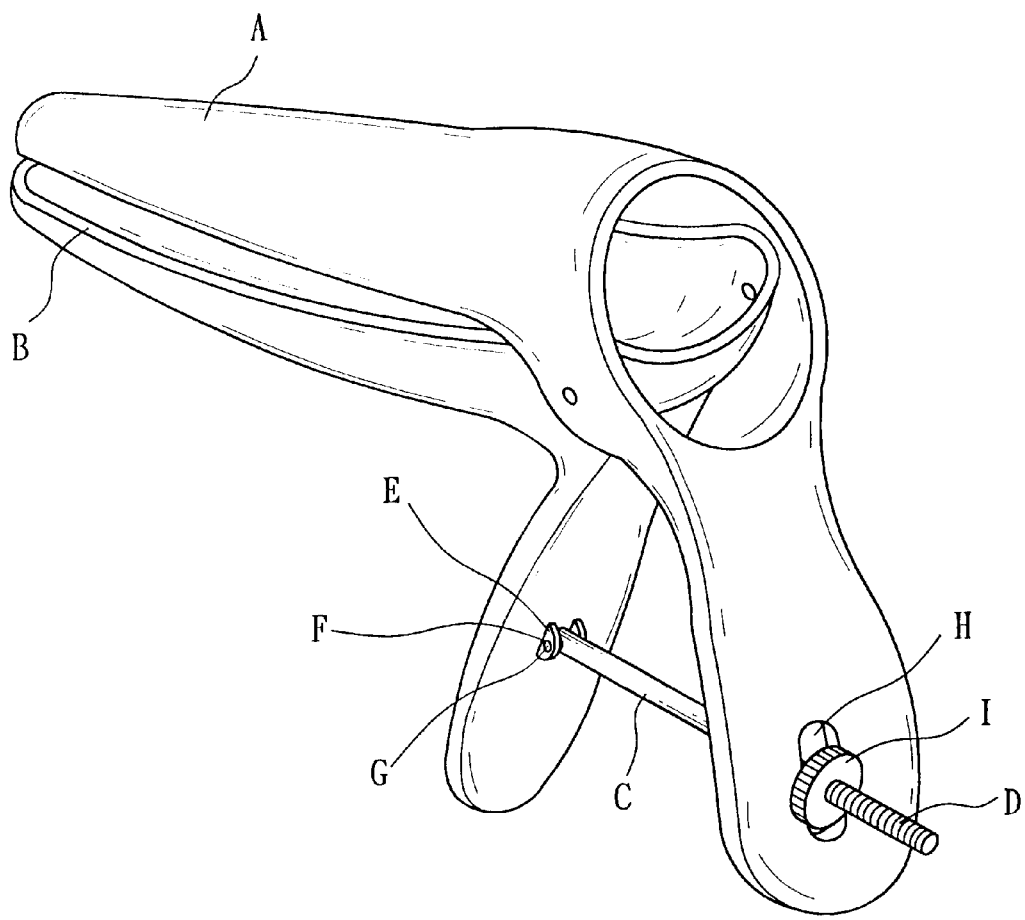
FIG. 1 is the external schematic diagram of the prior art of Vagina Speculum.
Figure 2:
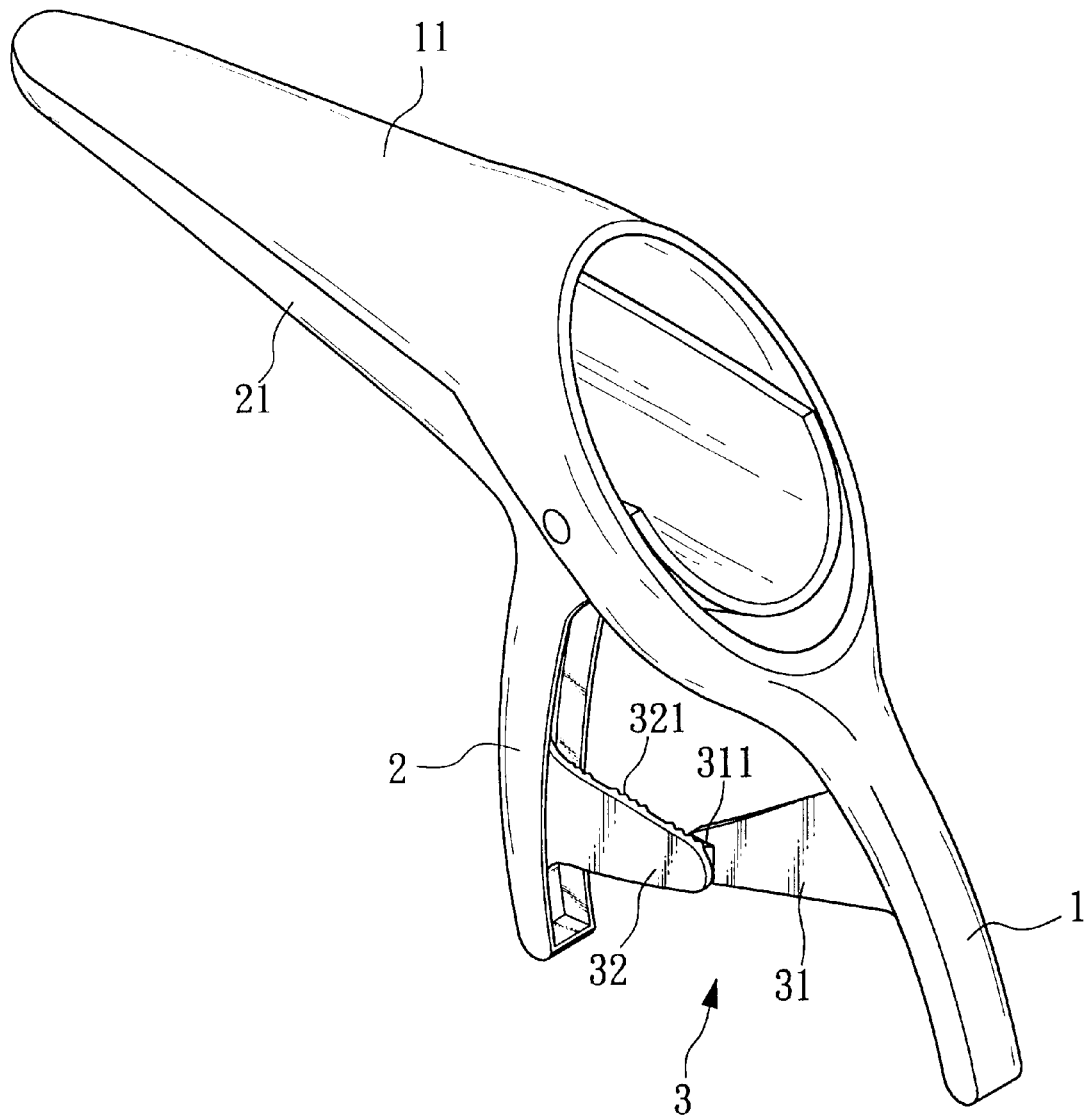
FIG. 2 is the external and three-dimensional diagram of the first preferred embodiment of the invention.

Firstly, please refer to FIG. 2. The structure of the invention consists of upper jaw 11 and lower jaw 21 with internal concave profiles at the front ends of a first body 1 and a second body 2. The first body 1 and the second body 2 are pivotally jointed together, and a buckling structure 3 is set on the first body 1 and the second body 2, which is held by a user to rapidly stretch and fasten the front ends of upper jaw 11 and lower jaw 21 of first body 1 and second body 2. The feature of the invention focuses on improving the buckling structure 3 for fast fastening and releasing functions. Thus, after application, the buckling structure may be quickly released due to the pressing force of patient's vagina applying on the upper jaw 11 and lower jaw 21 and the gentle releasing force of the pivoting joint of the first body 1 and the second body 2.

Figure 3:
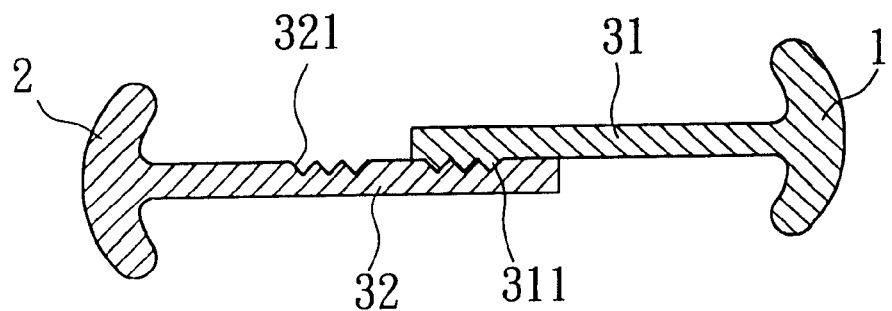
FIG. 3 is the schematic diagram of buckling structure of the first preferred embodiment of the invention.

The foresaid buckling structure 3 may have a variety of embodiments. Referring to FIGS. 2 and 3, the first preferred embodiment, wherein the buckling structure 3 of the invention is mainly comprised of a first buckling piece 31 and second buckling piece 32 protruding from the first body 1 and second body 2 respectively. A surface of the first buckling piece 31 has at least one protruding block 311 with saw teeth figure, and the internal surface on the second buckling piece 32 relative to the said internal surface of the first buckling piece 31 is set plural concave slots 321, partitioned by suitable distance, to match the foresaid protruding block 311. Thus, the merit for buckling structure 3 is to keep the invention more stable either in use or nonuse, without looseness.

When the improved Vagina Speculum is to be used, the front ends of the upper jaw 11 and lower jaw 21 are inserted into the patient's vagina, then the first body 1 and the second body 2 are opened to stretch the front ends of the upper jaw 11 and lower jaw 21. The protruding block 311 with saw teeth figure on the first buckling piece 31 engages the concave slot 321 with saw teeth figure on the second buckling piece 32. For removing the improved Vagina Speculum from vagina, gently push protruding block 311 to touch upon a flat surface between two concave slots 321 on the second buckling piece 32. Thus, protruding block 311 is against the second buckling piece 32 and the second buckling piece 32 is out of the concave slot 321. Furthermore, the pressing force of patient's vagina on the upper jaw 11 and lower jaw 21 and the gentle releasing force of pivoting joint of first body 1 and second body 2 are the factors of fast release according to the improved structure.

Figure 4:
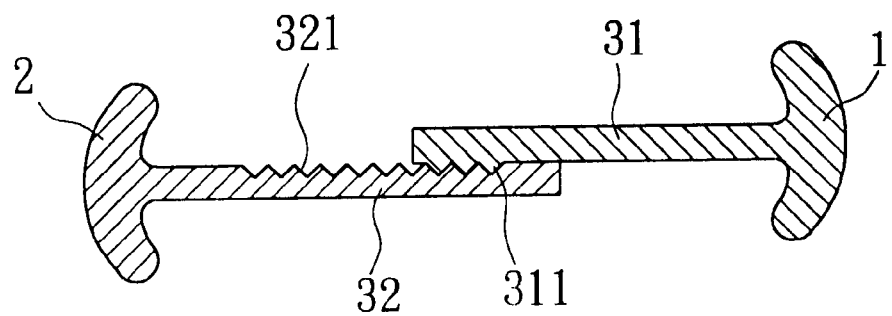
FIG. 4 is the schematic diagram of buckling structure of the second preferred embodiment of the invention.

FIG. 4 shows the second preferred embodiment. The concave slot on buckling piece 32 with saw teeth figure is a continuous design.

Figure 5:
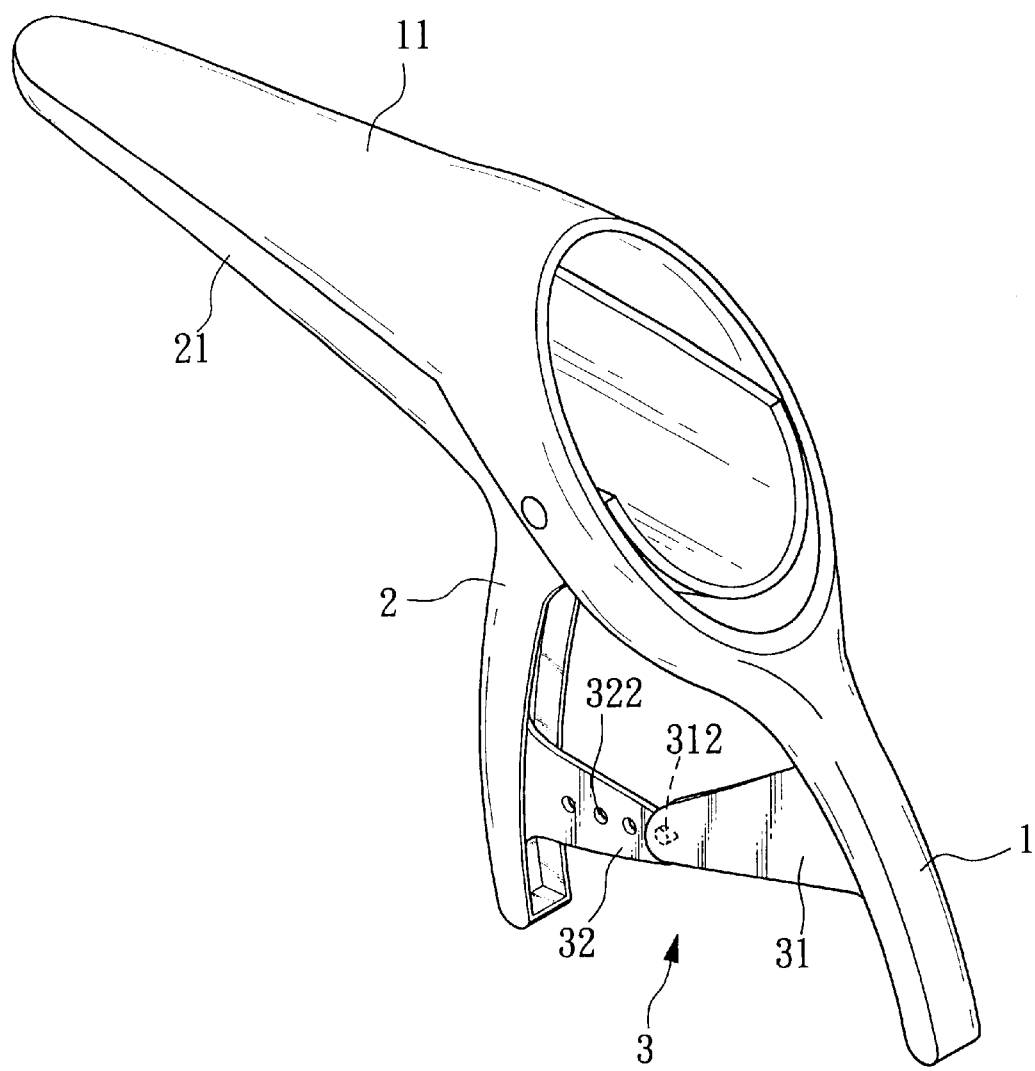
FIG. 5 is the external and three-dimensional diagram of the third preferred embodiment of the invention.
Figure 6:
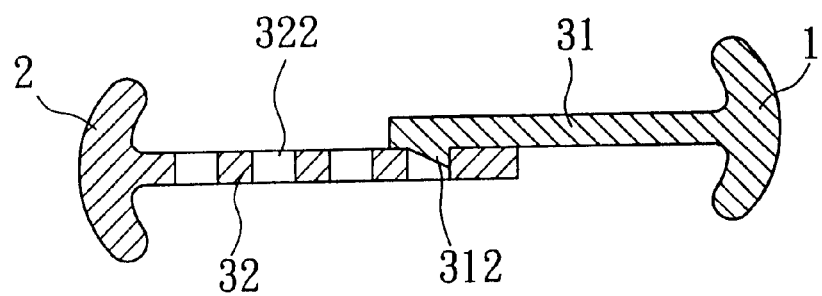
FIG. 6 is the schematic diagram of buckling structure of the third preferred embodiment of the invention.

FIG. 5 is the third preferred embodiment, wherein the buckling structure of the invention includes a first buckling piece 31 and second buckling piece 32 on the internal surfaces between the first body 1 and second body 2. There is at least one protruding block 312 on the surface of the first buckling piece 31, which has a slope top surface. The top surface of the protruding block 312 is lower on front end and higher on rear end, as shown in FIG. 6. The surface on the second buckling piece 32 relative to the foresaid surface of the protruding block 312 has several concavities 322 with suitable arrangement for matching the protruding block 312. The design of the buckling structure of the embodiment shown in FIG. 5 is an extension from the buckling structure shown in FIG. 2, hence, the merit of the design in FIG. 5 is same as the buckling structure shown in FIG. 2, which is to keep the invention more stable either in use or nonuse, without looseness.

The foresaid concave 322 could be bowl-shaped or hollow type.

Figure 13:
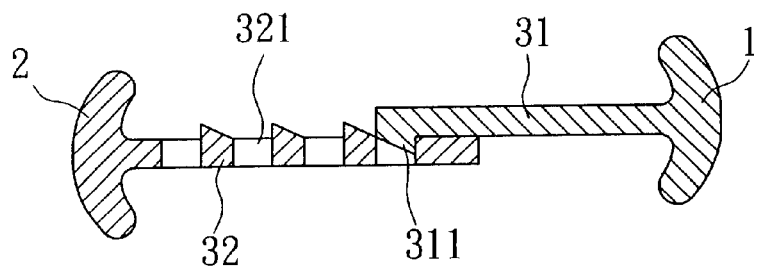
FIG. 13 is the schematic diagram of buckle structure of the fourth preferred embodiment of the invention.

The flat surface between concaves 322 could also be sloped as shown in FIG. 13.

When the improved Vagina Speculum is applied, the front ends of the upper jaw 11 and lower jaw 21 are put into patient's vagina, then holding and gripping the first body 1 and the second body 2 to stretch the front ends of the upper jaw 11 and lower jaw 21. The protruding block 312 on the first buckling piece 31 pushes the second buckling piece 32 until the protruding block 312 engages one of the concaves 322. To remove the improved Vagina Speculum from vagina, move the protruding block 312 onto the flat surface between the two concaves 322 on the second buckling piece 32. Furthermore, the pressing force of the patient's vagina on the upper jaw 11 and lower jaw 21 and the gentle releasing force of the pivoting joint of first body 1 and second body 2 are the factors to fast release the improved structure.

The foresaid buckling pieces 31 and 32 could also be cylindrical types. The connection relationship of the first buckling piece 31 with the second buckling piece 32 and the first body 1 with the second body 2 could be the foresaid fastening type, or could be another type in which at least one buckling piece is an active buckle to connect between the first body and the second body. Therefore, slightly pushing the said active buckling piece to separate a protruding block on another buckling piece from a concave on the active buckling piece, and the purpose of fast releasing is then reached.

Figure 7:
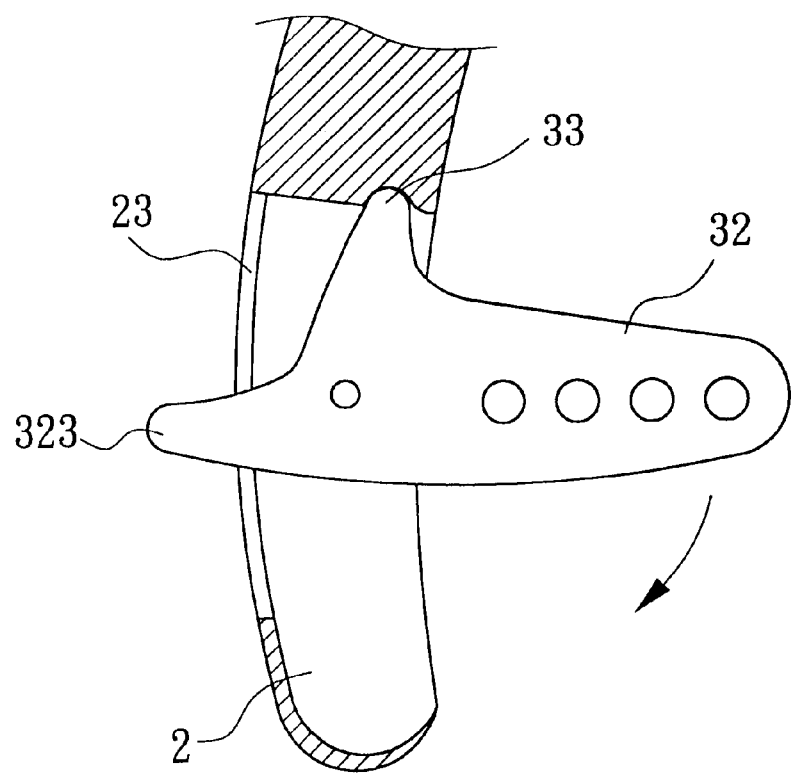
FIG. 7 is the schematic diagram of transverse section of action buckling piece of the first preferred embodiment of the invention.
Figure 8:
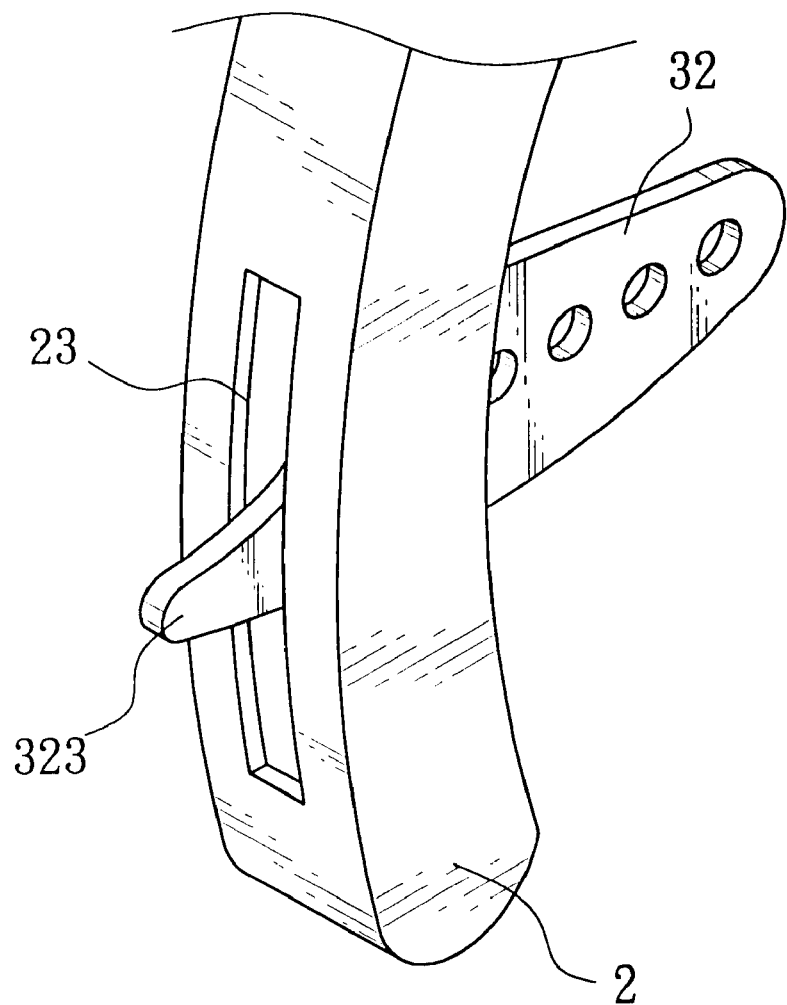
FIG. 8 is the external and three-dimensional diagram of active buckling piece of the first preferred embodiment of the invention.

The design of active buckling piece may include many different embodiments, of the following descriptions: firstly, it is joint swing type, with a slot 23 on the second body 2, thus, the second buckling piece 32 is fastened on the second body 2 pivotally (shown in FIGS. 7 and 8). A protruding rim 323 on one end of the second buckling piece 32 slightly protrudes from the outer rim of the second body 2. Between the second buckling piece 32 and the second body 2 is a matching structure 33, having the roles of connecting and fastening the second buckling piece 32 and the second body 2 before operating the second buckling piece 32. The only way to fast release after operation is pivoting the second buckling piece 32.

Figure 9:
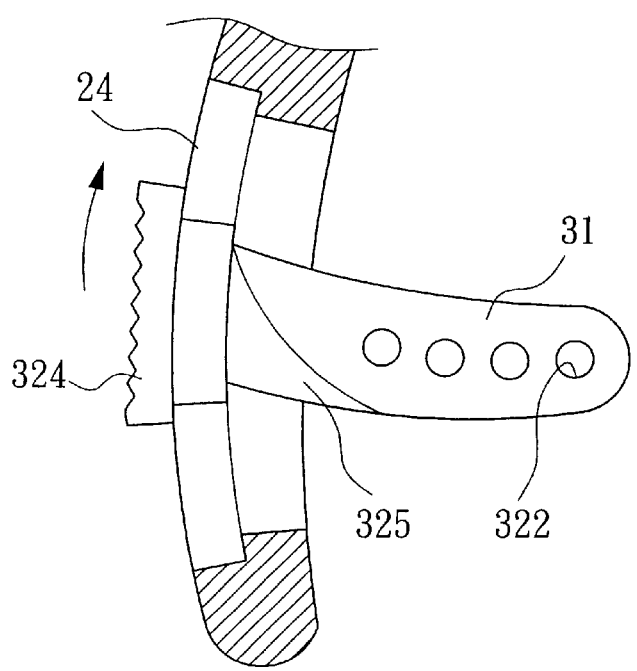
FIG. 9 is the schematic diagram of active buckling piece of the second preferred embodiment of the invention.
Figure 10:
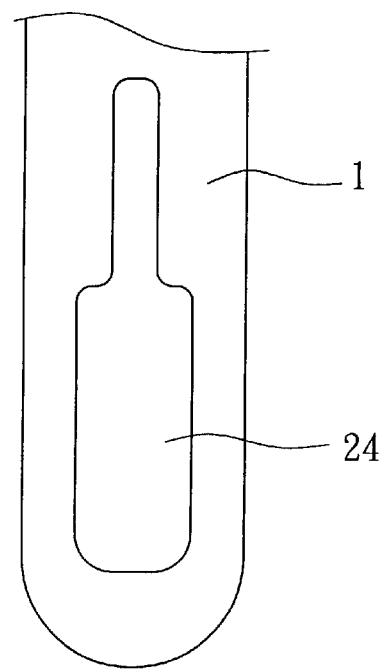
FIG. 10 is the schematic diagram in another direction of active buckling piece of the second preferred embodiment of the invention.

Furthermore, another design is that an aperture 24 is set on the outside of the first body 1 (shown in FIGS. 9 and 10). Meantime, there is at least one roughened protruding part 324 set on the first buckling piece 31, and that is to let the first buckling piece 31 insert into an aperture 24 through the body to move up and down by hand in the aperture. Also, the protruding part 324 set on the first buckling piece 31 could protrude outside of the first body and the rough surface of the protruding part 324 is to increase friction for convenient movement. There is a slope 325 designed on a surface, of the first active buckling piece 31 (shown in FIG. 9) of the first body 1. The slope 325 is located on the connection area of the first active buckling piece 31. Hence, when the second buckling piece contacts the slope 325, the first active buckling piece 31 is pushed down to be out of connection with the second active buckling piece 32.

Figure 14:
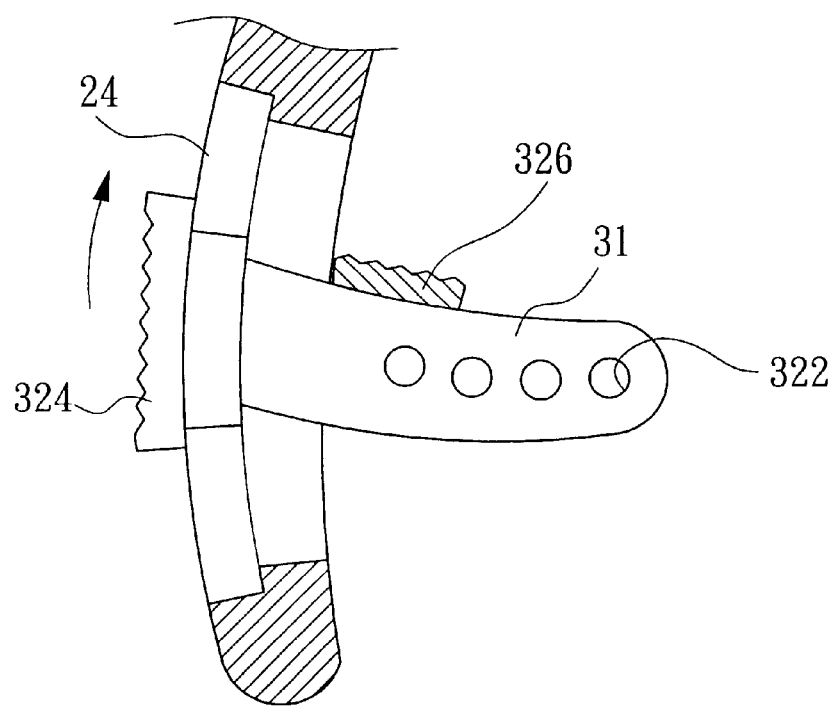
FIG. 14 is the schematic diagram of buckle structure of the fifth preferred embodiment of the invention.

Another design (shown in FIG. 14) is to add a pressing plate 326 for forefinger or middle finger handling. The active buckling piece is convenient to be pressed down as well.

Figure 11:
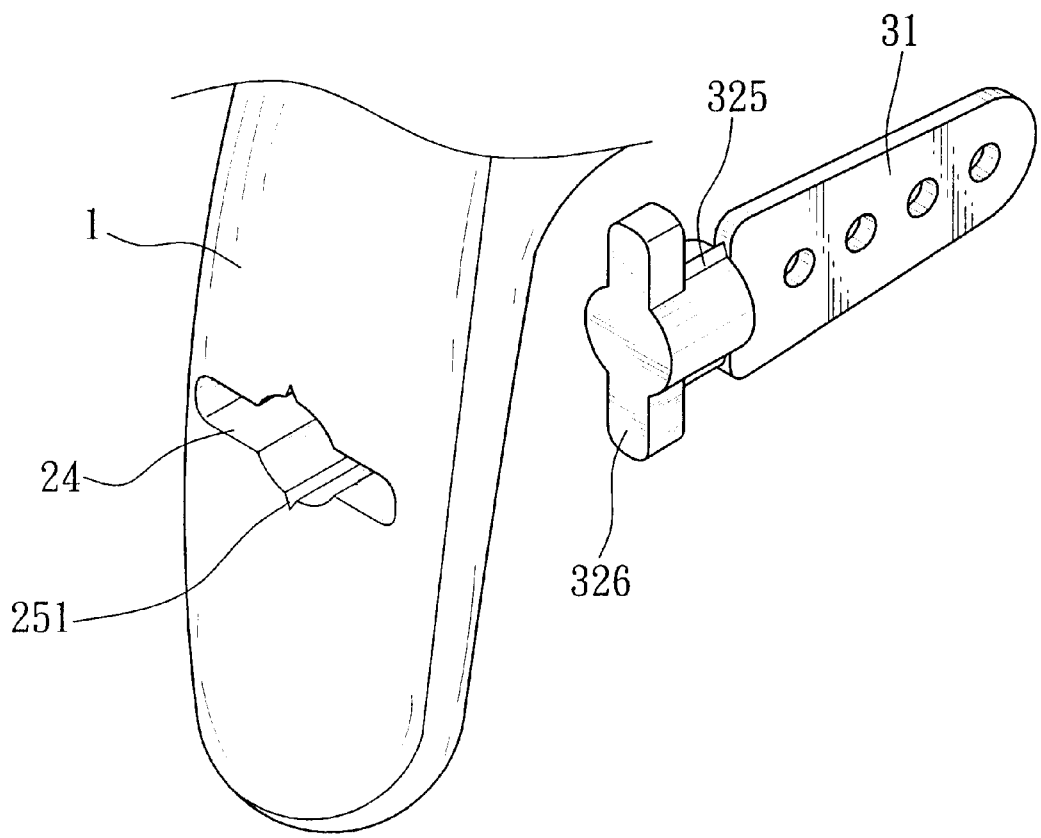
FIG. 11 is the schematic diagram of active buckling piece of the third preferred embodiment of the invention.

The invention also could have another design, a fitting structure designed on both internal profile of an aperture and external profile of a front head of an active buckling piece, actually that is shown in FIG. 11. The aperture 24 could be gone through by the front head of the first buckling piece 31. The internal rim of the aperture 24 has a concave slot 251, and the first buckling piece 31 has a protruding rim 325. Thus, the concave slot 251 and the protruding rim 325 cooperatively engage each other. The function in operation for the foresaid concave slot 251 and protruding rim 325 is to maintain a suitable angle for the first buckling piece 31. Besides, the said buckling piece is assembled at least one protruding part, and the protruding part 326 bulges outside of the first body 1 for the user's handling. After operation, the user can directly turn the protruding part 326 to a suitable angle for fast releasing.

Figure 15:
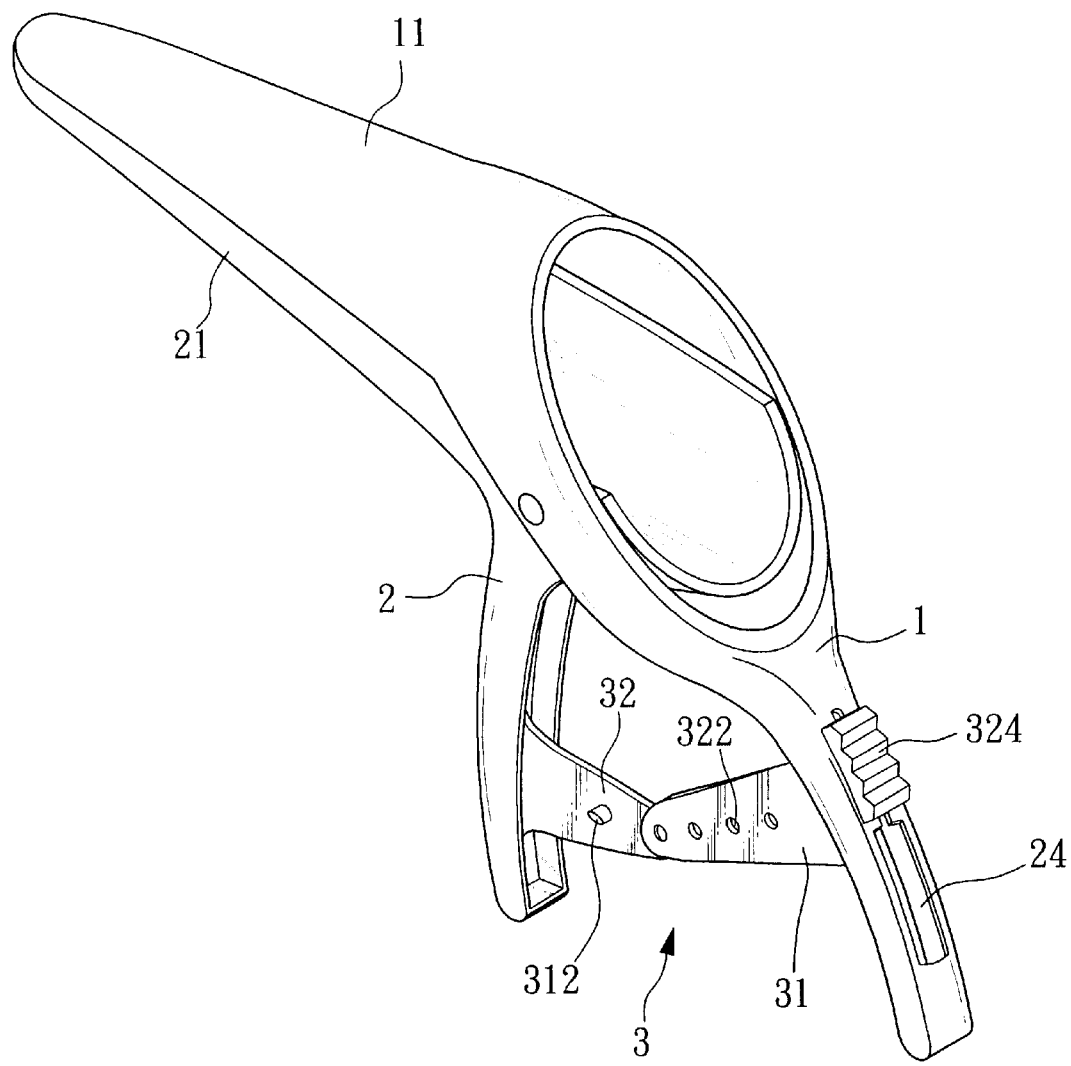
FIG. 15 is the schematic diagram of buckle structure of the sixth preferred embodiment of the invention.

The design shown as FIG. 5 with the foresaid active buckling type could be re-designed as shown in FIG. 15. Therefore, user can easily handle the roughened protruding part 324 by a thumb.

Figure 12:
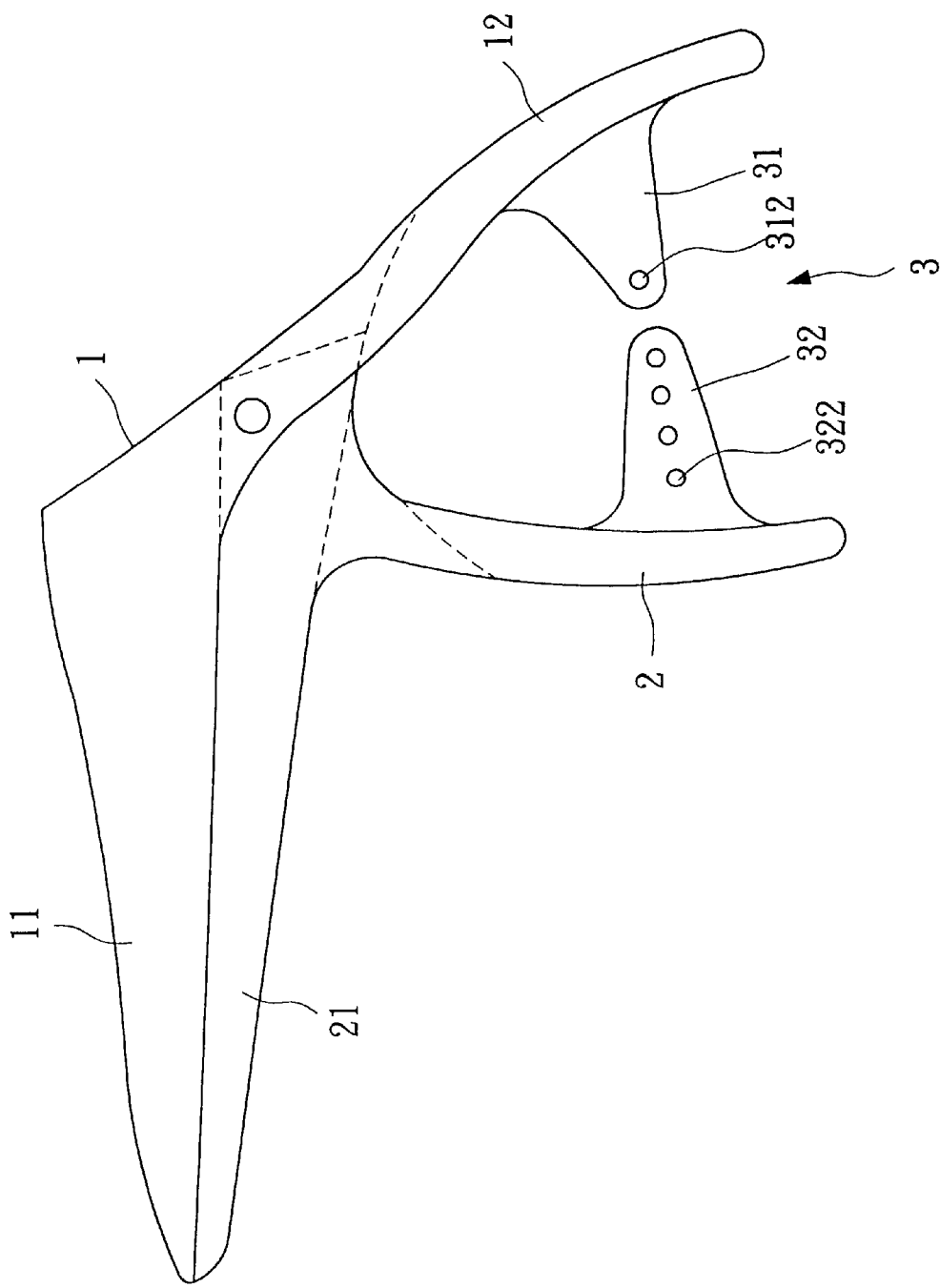
FIG. 12 is the plan view of the invention.

Another embodiment of the invention is to extend the length of the end of lower jaw for the second body 2 (shown in FIG. 12). Thus, the end of lower jaw protrudes to the outside of a handle 12 below part of the first body I when operating. The benefit from the embodiment is that patient's secretion goes along the extended end of the lower jaw 21 to drain out and does not drop onto the handle 12.

The positions for the foresaid protruding block and the cooperated concave slot on the first buckling piece and the second buckling piece could be exchanged.

The top surface of the upper jaw 11 of the first body and the bottom surface of the front end of the lower jaw 21 have a curvature between 40 to 50 millimeter (Radius =40~50 mm). The connection rims of convex external profiles of the first body 1 and the second body 2 show the two bodies are vertical or almost vertical to an imagine connection plane of upper jaw 11 and lower jaw 21, and the angle value is between 80 and 90 degrees.

The above-mentioned preferable embodiments are applied to describe the present invention in detail, however, they are not the limited scope of the present invention. Any changed for the content of the invention to produce the effects and features similar to the above mentioned embodiments and constructed by the people who are familiar with the technology will belong to the scope of the present invention.

As a conclusion, the invention of the improved structure for Vagina Speculum possesses the features of simplified structure and easy manufacturing, furthermore, it is not only that improving the inconvenience of releasing and closing of prior art, but also avoiding secretion dropping onto handle.

What the claim is:

1. An improved vaginal speculum comprising:
   a) a first body having a front upper jaw portion, a middle portion having an opening and a first handle portion extending from the middle portion;
   b) a second body having a front lower jaw portion and a second handle portion, the second body pivotally connected to the first body such that the upper and lower jaw portions are adjacent to each other when in a closed position, the first and second bodies being movable between closed and open positions;
   c) an aperture extending through one of the first and second handle portions from an exterior to an interior thereof;
   d) a first buckling member movably located in the aperture and having a first inner portion extending from the interior of the handle portion having the aperture toward the other handle portion;
   e) a second buckling member fixedly mounted on an interior of the handle portion without the aperture and having a second inner portion extending toward the handle portion having the aperture, the first and second inner portions being adjacent to each other when the first and second bodies are in the open position; and,
   a fastening device including a protruding block extending from one of the first and second inner portions engaging a recess in the other of the first and second inner portions, such engagement holding the first and second bodies in the open position.

2. The improved vaginal speculum of claim 1 wherein the fastening device further comprises a plurality of recesses.

3. The improved vaginal speculum of claim 1 wherein the first and second inner portions have elongated, planar configurations.

4. The improved vaginal speculum of claim 1 wherein the first buckling member is slidably mounted in the aperture.

5. The improved vaginal speculum of claim 4 further comprising a slope surface formed on the first buckling member.

6. The improved vaginal speculum of claim 1 further comprising a protruding part on the first buckling member located on an exterior of the associated handle portion.

7. The improved vaginal speculum of claim 6 wherein the protruding part includes a rough external surface portion.

8. The improved vaginal speculum of claim 1 wherein the first buckling member is rotatably mounted in the aperture.

9. The improved vaginal speculum of claim 8 further comprising:
   a) slots located on opposite sides of the aperture; and,
   b) protruding rims on the first buckling member located so as to engage the slots.

* * * * *